United States Patent [19]

Hope

[11] Patent Number: Plant 5,669

[45] Date of Patent: Feb. 18, 1986

[54] KALANCHOE PLANT NAMED CALIENTE

[75] Inventor: Claude Hope, Cartago, Costa Rica

[73] Assignee: Pan American Plant Company, Parrish, Fla.

[21] Appl. No.: 594,490

[22] Filed: Mar. 27, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Kalanchoe plant which has a compact growth habit, yet is freely branched, and bears red-orange flowers.

1 Drawing Figure

1

The present invention relates to a new and distinctive cultivar of Kalanchoe plant, botanically known as Kalanchoe named Caliente.

The new cultivar was referred to during the selection process by the designation (Red Glow-1-4-1-4 × Swiss Glistening Orange -2-1-4-1)-2-2-26, and is a product of a planned breeding program. Caliente was later recoded KLV80-92R when received by Pan American Plant Co., West Chicago, Ill. in 1980. The basic objective of the breeding program was to create a new kalanchoe cultivar having red-orange flowers, compact and floriferous habits, and the ability to produce commercially acceptable quality in a year round kalanchoe program.

The new cultivar was originated from a self-pollination of the cultivar (Red Glow -1-4-1-4 × Swiss Glistening Orange -2-1-4-1)-2-2 made in a controlled breeding program at Linda Vista S.A. Cartago, Costa Rica.

Caliente was discovered and selected by me or a technician working under my direction, as a flowering plant within the progeny of the stated self in a field of seedlings in Cartago, Costa Rica. Asexual reproduction of the new cultivar by stem cuttings, as performed by me at Pan American Plant Co., West Chicago, Ill. and Parrish, Fla., has demonstrated that the combination of characteristics as herein disclosed for the new cultivar are firmly fixed and are retained through successive generations of asexual reproduction.

Caliente has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Caliente, which in combination distinguish this Kalanchoe as a new and distinct cultivar:

(1) Bright red-orange flower color.

(2) Compact habit and average growth rate as compared to other cultivars of this type.

(3) Freely branching with shoots formed at every node.

(4) Suitable for production in 10–15 cm. pots, and it flowers in 11 weeks under favorable conditions, to 14 weeks under less favorable growing conditions.

(5) Highly floriferous, with numerous flowers formed at every shoot.

2

(6) To reduce peduncle elongation after flower initiation plants can be treated with B-9.

(7) When grown under high light/temperatures younger foliage may be edged in brick red.

The new cultivar is most similar to the commercially available cultivar Red Sunrise. Caliente is principally distinguished from Red Sunrise by its more orange flower color and two week earlier flower response under high temperatures.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 7000 ft. candles of natural light at approximately 9:30 A.M. in Parrish, Fla.

Botanical classification: Kalanchoe, cv. Caliente.

Parentage: Self-pollination of the cultivar (Red Glow 1-4-1-4 × Swiss Glistening Orange 2-1-4-1)-2-2.

Propagation: The new cultivar holds its distinguishing characteristics through successive propagations by leaf cuttings and by division of shoots.

A. *Type cutting.*—Tip cuttings with stems up to 2 cm. long.

B. *Time to root.*—10 days at 21° C. summer to 14 days at 21° C. winter.

C. *Rooting habit.*—Fibrous, many very fine roots.

Plant description:

A. *Form.*—Upright, compact, growing and scheduling practices can produce small plants in 10 cm. pots or large plants in 15 cm. pots.

B. *Habit of growth.*—Average growth rate for this type of plant. Shoots are formed at every node.

C. *Foliage description.*—Leaves simple, opposite, generally symmetrical. 1. Size: Average full grown leaf of a flowering plant in a 10 cm. pot is 10–11 cm. long and 55–65 mm. wide. Plants in larger pots have larger full grown leaves. 2. Shape: Ovate, apex acute to obtuse and base is acute. 3. Texture: Glabrous, coriaceous, succulent. 4. Margin: Crenate, irregular. 5. Color: Young foliage top side, 137B, under side, 137C. Mature foliage top side 137A, under side 137C.

Flowering description:

A. *Flowering habit.*—Inflorescence of each shoot is formed by dichotomous branching, starting with opening of the terminal flower of the main axis, followed by terminal flowers of the side branches of the inflorescence. Opening of new buds will continue for 2 months or more. Individual flowers will last two weeks or more after opening.

B. *Natural flowering season.*—January. Flowering time under controlled daylength at 32° C. in summer is 14 weeks; in winter at 21° C., 11 weeks. Flowering time depends on temperature, light intensity and other growing conditions.

C. *Flower buds.*—Oblong developing to tubular as petals mature. Sheathed by 4 green sepals. Corolla at maturity is about 15 mm. long. (1) Size: Up to 15 mm. long. (2) Shape: Oblong. (3) Rate of opening: Normal.

D. *Flower borne.*—Compound dischasial cyme on strong peduncles. Peduncle length depends upon growing conditions and B-9 application. Pedicels up to 7 mm. long.

E. *Quantity of flowers.*—Very floriferous, with new flowers continuing to develop.

F. *Petals.*—(1) Shape: Obovate, apex cuspidate. (2) Color: Top side when opening, 44B, with little or no fading; under side, 33C. (3) Number and size of petals: 4, united in corolla; petals 5 mm. in diameter, total flower diameter up to 2 cm.

G. *Reproductive organs.*—(1) Stamens: 8 in number. (a) Anther shape: Flat, ellystial. (b) Filament color: Yellow. (c) Pollen color: Yellow. (2) Pistils: (a) Stigma shape: Flat, crystalline. (b) Style color: Greenish-white. (c) Ovaries: 4 celled, 8 mm. long, green.

Disease resistance: No known Kalanchoe diseases observed to date.

General observations: Caliente is a new and distinct Kalanchoe cultivar particularly characterized by an abundance of red-orange flowers, and its compact and freely branching habit. An extra application of growth regulator may be required to control the peduncle length and keep the plant more compact. The foliage is sometimes edged with brick red when the cultivar is grown under high light or high temperatures. This variety has an average 12 week flowering response and is adaptable to produce in 10–15 cm. pots.

I claim:

1. A new and distinct cultivar of Kalanchoe plant named Caliente, as described and illustrated, and particularly characterized by its bright red-orange flower color, compact growth habit, free branching, highly floriferous habit, and by its adaptability to production in 10–15 cm. pots.

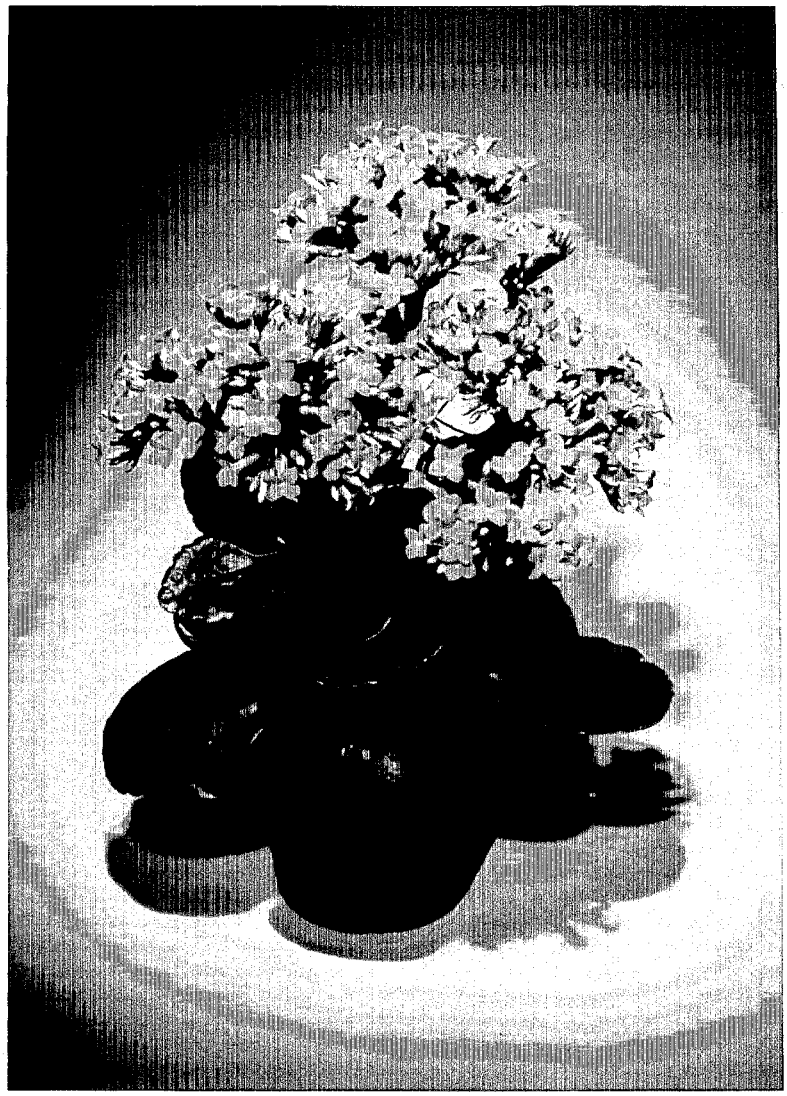

* * * * *